United States Patent
Palle et al.

(10) Patent No.: US 8,614,225 B2
(45) Date of Patent: Dec. 24, 2013

(54) PROCESS FOR THE PURIFICATION OF PALONOSETRON OR ITS SALT

(75) Inventors: Raghavendracharyulu Venkata Palle, Hyderabad (IN); Madhavrao Marathe Anant, Hyderabad (IN); Nageshwar Gunda, Mahaboob Nagar (IN)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 1555 days.

(21) Appl. No.: 11/846,055

(22) Filed: Aug. 28, 2007

(65) Prior Publication Data

US 2008/0058367 A1 Mar. 6, 2008

Related U.S. Application Data

(60) Provisional application No. 60/868,955, filed on Dec. 7, 2006.

(30) Foreign Application Priority Data

Aug. 30, 2006 (IN) ............................ 1564/CHE/2006

(51) Int. Cl.
*C07D 221/06* (2006.01)
*A61K 31/435* (2006.01)

(52) U.S. Cl.
USPC .......................................... 514/296; 546/98

(58) Field of Classification Search
USPC .......................................... 546/98; 514/296
See application file for complete search history.

(56) References Cited

U.S. PATENT DOCUMENTS

| 5,202,333 A | 4/1993 | Berger |
| 5,510,486 A | 4/1996 | Robinson |
| 5,567,818 A | 10/1996 | Kowalczyk |

FOREIGN PATENT DOCUMENTS

| WO | 2008/051564 A2 | 5/2008 |
| WO | 2008/073757 A1 | 6/2008 |
| WO | 2009/087643 A1 | 7/2009 |

OTHER PUBLICATIONS

Abstract Trissel Lawrence 2004, Physical and Chemical Stability of Palnosetron.*
R. D. Clark et al., "2-(Quinuclidin-3-yl)pyrido[4,3-b]indol-1-ones and Isoquinolin-1-ones. Potent Conformationally Restricted 5-HT3 Receptor Antagonists," Journal of Medicinal Chemistry, vol. 36, pp. 2645-2657, 1993.
Anonymous, US Pharmacopeia Test Method USP 29, [online], [retrieved on Aug. 25, 2011]. Retrieved from the Internet <URL: http://www.pharmacopeia.cn/v29240/usp29nf24s0_c941.html>.
Suryanarayanan, Raj, "Chapter 7, X-Ray Powder Diffractometry", in Physical Characterization of Pharmaceutical Solids, Brittain, Harry G., ed., Marcel Dekker, Inc., New York, 1995, p. 187-221.
Gavezzotti, Angelo, "Are Crystal Structures Predictable?", Acc. Chem. Res., 1994,27,309-314.
Gavezzotti, Angelo, "Ten years of experience in polymorph prediction: what next?", CrystEngComm, 2002, 4(61), 343-347.

(Continued)

*Primary Examiner* — Rita Desai
(74) *Attorney, Agent, or Firm* — Pergament Gilman & Cepeda LLP; Milagros A. Cepeda; Edward D. Pergament

(57) ABSTRACT

The present application relates to a process for purification of palonosetron or its salt substantially free of its R-isomer and structure related impurities.

13 Claims, 3 Drawing Sheets

(56) References Cited

OTHER PUBLICATIONS

Day, Graeme M., et al., (2006) "Investigating the latent polymorphism of maleic acid," Chemical Communications 1 (1): 54-56.
Thallapally, Praveen K., (2004) "Polymorphism of 1,3,5-Trinitrobenzene Induced by a Trisindane Additive," Angewandte Chemie International Edition, 43 (9): 1149-1155.
Rouhi, A.M., "The Right Stuff," Chemical and Engineering News, vol. 81, No. 8, pp. 32-35, Feb. 24, 2003.
Goho, A., "Tricky Business" Science News, vol. 166, No. 8, pp. 122-124, Aug. 21, 2004.
Brittain, Harry G., "Chapter 6 Methods for the Characterization of Polymorphs and Solvates", in "Polymorphism in Pharmaceutical Solids", Brittain, Harry G. ed., Marcel Dekker, Inc. New York, 1999, p. 227-278.

* cited by examiner

PROCESS FOR THE PURIFICATION OF PALONOSETRON OR ITS SALT

FIELD OF THE APPLICATION

The present application relates to a process for purification of palonosetron or its salt.

BACKGROUND OF THE APPLICATION

Palonosetron is the adopted name for a drug compound having the chemical name (3aS)-2-[(S)-1-azabicyclo[2.2.2]oct-3-yl]-2,3,3a,4,5,6-hexahydro-1-oxo-1H-benz[de]isoquinoline and is represented by the structural Formula I.

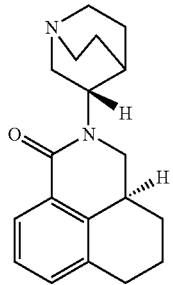

Formula I

Palonosetron hydrochloride is an antiemetic and antinauseant agent and is available in the market under the brand name "ALOXI" in the form of injection. Each vial contains palonosetron hydrochloride equivalent to 0.25 mg of base.

There is a need to provide efficient purification process to produce the palonosetron hydrochloride of Formula I which is substantially free of structure related and other unwanted isomer impurities.

SUMMARY OF THE APPLICATION

According in one embodiment the present invention provides a purification process to produce palonosetron or its salt with substantially free of structure related and isomeric impurities, which process is simple, cost-effective, and well suited for use on an industrial scale.

Another embodiment of the present invention is to provide palonosetron or its salt having purity equal to or greater than 99.5%.

In an embodiment, the present invention provides palonosetron or its salt having R-isomer content less than 0.2%.

In another embodiment, the present invention provides palonosetron or its salt having 2-[(S)-1-Azabicyclo[2.2.2]oct-3-yl]-2,4,5,6-tetrahydro-1H-benz[de]isoquinolin-1-one-.hydrochloride (hereinafter referred to as "PAL-3") content less than 0.2%.

In an embodiment, the present invention provides palonosetron or its salt having less than 0.2% of each of the R-isomer content and PAL-3.

An embodiment of the present invention relates to a process for purification of palonosetron or its salt substantially free of its R-isomer and structure related impurities.

In another embodiment, the present invention provides the crystalline form of palonosetron hydrochloride resulting from the present process is characterized X-ray powder diffraction (XRPD) pattern substantially in accordance with FIG. 1. having the principal peaks approximately at 7.1, 13.8, 14.2, 15.8, 18.5, 19.7, 20.0 and 24.4±0.2 degrees 2 theta.

In another embodiment, the present invention provides the crystalline form of palonosetron hydrochloride obtained by the present process has an endotherm peak at 306.83° C. by differential scanning calorimetry (DSC), which is substantially in accordance with FIG. 2.

In another embodiment, the present invention provides a process for purification of palonosetron having purity greater than or equal to 99.5% of palonosetron or its salt, said process comprising:

In another embodiment, the present invention provides a process for purification of palonosetron having purity greater than or equal to 99.5% of palonosetron or its salt, wherein the solvent is methanol or ethanol.

In another embodiment, the present invention provides a reprocessing process for purification of palonosetron or its salt wherein the content of PAL-3 in said palonosetron or its salt is more than 1%, said process comprising:

(a) reducing palonosetron or its salt in the presence of a suitable reducing agent; and (b) optionally, recrystallizing the compound obtained in step a) in alcohol.

Another embodiment of the present invention provides a pharmaceutical composition comprising crystalline form of palonosetron along with one or more pharmaceutically acceptable excipients.

In another embodiment of the present invention, there is provided pharmaceutical compositions comprising crystalline forms of palonosetron, which are useful in the treatment of disease.

In another embodiment of the present invention, there is provided pharmaceutical compositions comprising crystalline forms of palonosetron, which are useful in the treatment of emesis.

DETAILED DESCRIPTION OF THE APPLICATION

Figure 1:
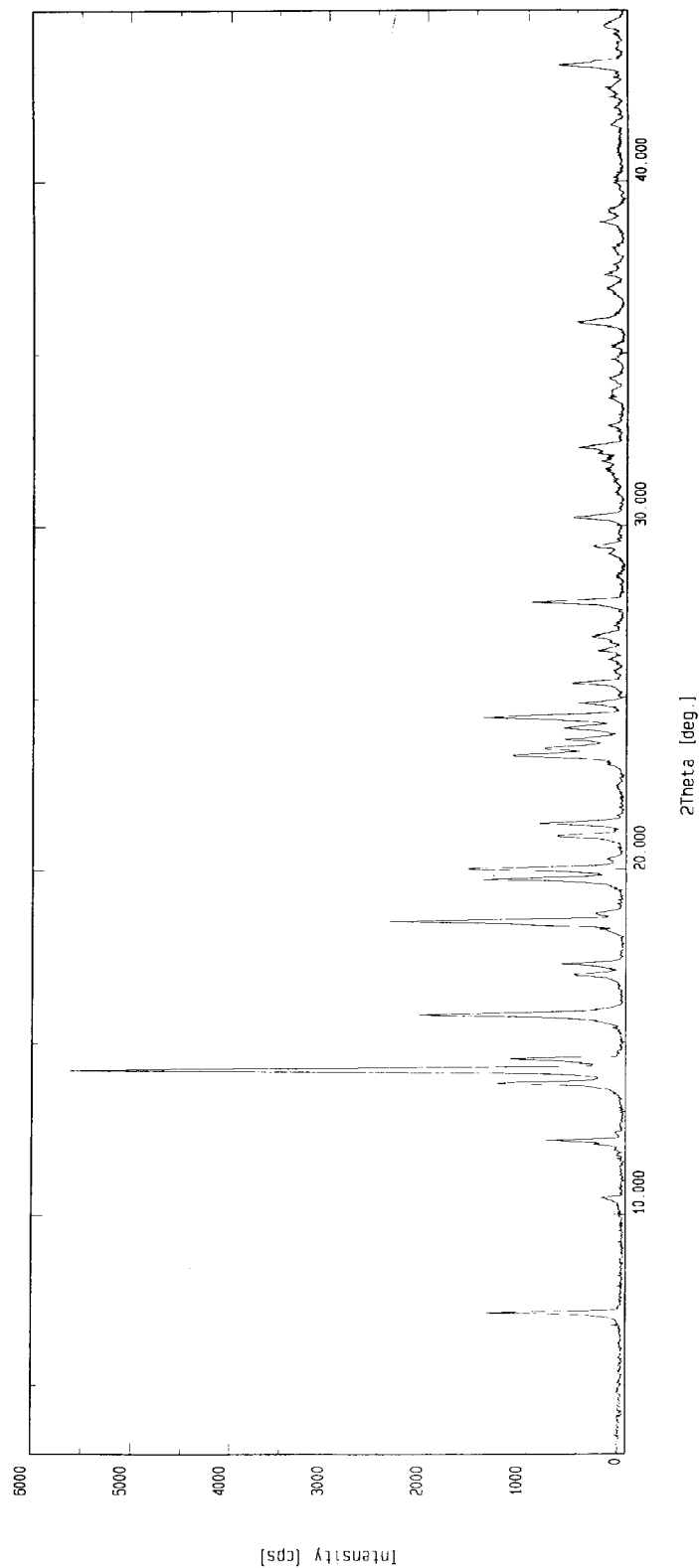
FIG. 1 is an X-ray powder diffraction (XRPD) pattern of palonosetron hydrochloride crystalline form prepared according to Example 3.

An embodiment of the present invention relates to a process for purification of palonosetron or its salt substantially free from its R-isomer and structure related impurities.

An embodiment of the present invention is to provide palonosetron or its salt having purity equal to or greater than 99.5%.

In one embodiment, the present invention provides palonosetron or its salt having R-isomer content less than 0.2%.

In another embodiment, the present invention provides palonosetron or its salt having 2-[(S)-1-Azabicyclo[2.2.2]oct-3-yl]-2,4,5,6-tetrahydro-1H-benz[de]isoquinolin-1-one.hydrochloride (PAL-3) content is less than 0.2%.

In another embodiment, the present invention provides a process for getting purity greater than or equal to 99.5% of palonosetron or its salt, said process comprising:

(a) providing a solution of palonosetron or its salt in a solvent;

(b) isolation of solid from the solution obtained in step a); and (c) optionally, drying the solid.

Step (a)—Providing a Solution of Palonosetron or its Salt in a Solvent.

Palonosetron or its salt may be obtained using any of the processes described in the art. The hydrochloride salt may be obtained by following a process similar to the one described in U.S. Pat. No. 5,202,333.

The solution of palonosetron or its salt can be obtained by the dissolution of palonosetron in a solvent. In an embodiment of the present invention the solvent is methanol, ethanol or mixtures thereof. Any form of palonosetron or its salt, such as anhydrous crystalline, amorphous, crystalline hydrate, or mixtures of amorphous and crystalline forms of palonosetron or its salt in any proportions obtained by any method; is acceptable for forming the solution.

The concentration of palonosetron or its salt in the solution is not critical, but the quantity of solvent employed is usually kept to a minimum so as to avoid excessive product losses during the crystallization of solid. The concentration of palonosetron or its salt in the solution may generally range from about 0.01 to about 1 g/ml in the solvent.

Palonosetron or its salt is mixed with sufficient amount of the solvent to provide solution of palonosetron or its salt at or below the reflux temperature of the solvent. Optionally, the solution obtained above can be filtered to remove the undissolved particles followed by further processes.

The solution can be filtered by passing through paper, glass fiber, or other membrane material, or a clarifying agent such as celite. Depending upon the equipment used and the concentration and temperature of the solution, the filtration apparatus may need to be preheated to avoid premature crystallization.

Step (b)—Isolation of Solid from the Solution Obtained in Step (a);

Suitable techniques used for isolation include techniques of crystallization, slurrying, or trituration in a suitable solvent.

Optionally, crystallization may be enhanced by methods such as cooling, partial removal of the solvent from the solution, seeding, adding an anti-solvent to the reaction mixture, or a combination thereof.

Partial removal of solvent may be carried out suitably using evaporation, atmospheric distillation or distillation under vacuum.

Distillation of the solvent may be conducted under a vacuum of about 100 mm Hg to about 720 mm Hg at a temperature of about 40° C. to about 70° C. Any temperature and vacuum conditions can be used as long as concentration occurs without increase in the impurity levels.

Concentration of the solution can be carried out to an extent where the precipitation of the palonosetron or its salt begins from the solution, converting the solution into slurry. Generally, concentration will be terminated when the ratio of solvent to palonosetron or its salt becomes about 1:1 to about 1:5.

The reaction mixture may be maintained further at a temperature lower than the concentration temperatures such as, for example, below about 40° C., for a period of time as required for a more complete isolation of the product. The exact cooling temperature and time required for complete crystallization can be readily determined by a person skilled in the art and will also depend on parameters such as concentration and temperature of the solution or slurry.

The obtained precipitate separates from the solution. One skilled in the art may appreciate that there are many ways to separate the solid from the mixture, for example it can be separated by using any techniques such as filtration by gravity or by suction, centrifugation, decantation, and the like. After separation, the solid may optionally be washed with suitable solvent such as methanol.

Step (c)—Optionally Drying the Solid.

The wet solid may optionally be further dried. Drying can be suitably carried out in a tray dryer, vacuum oven, air oven, fluidized bed drier, spin flash dryer, flash dryer and the like. The drying may be carried out at temperatures of about 35° C. to about 70° C. The drying can be carried out for any time periods necessary for obtaining a desired purity, such as from about 1 to about 25 hours, or longer.

Optionally, the above recrystallization process may be repeated one or more times to get a purity typically equal to or greater than about 99.5%, or about 99.8%, by weight as determined using HPLC.

Palonosetron or its salt obtained from the present purification contains less than about 0.2% of individual impurities such as R-isomer and PAL-3.

In another embodiment, the present invention provides a reprocessing process for purification of palonosetron or its salt wherein the Palonosetron or its salts has a PAL-3 content more than 1% to afford purity equal to or greater than about 99.5%, said process comprising:

a) reducing palonosetron or its salt in the presence of a suitable reducing agent; and b) optionally, recrystallization of the compound obtained in step (a) in alcohol.

Step (a)—Reduction of Palonosetron or its Salt.

Suitable reducing agents can be palladium catalysts like 5% Pd/C, 10% Pd/C, 20% Pd/C, palladium/BaSO4 and the like under aqueous or non-aqueous conditions.

The concentration of the catalyst can be determined based on the type of catalyst and the medium in which it is to be provided.

The pressure for the preparation of the solution can range from about 50 to 100 psi or more by using hydrogen gas.

The reduction can be carried out at a temperature of about 25° C. to about 100° C. or at a temperature of about 50° to about 65° C.

Suitable solvents which can be used for the reduction of palonosetron or its salt having PAL-3 content is more than 1% include, but are not limited to; alcoholic solvents like methanol, ethanol, isopropyl alcohol and the like; ketonic solvents such as acetone, ethylmethyl ketone, methyl isobutyl ketone and the like; hydrocarbon solvents such as toluene, xylene and the like; nitrile solvents such as acetonitrile, propionitrile and the like; or mixtures thereof.

After completion of the reaction, the reaction solution can be recovered by any of techniques such as filtration or decantation and then the obtained reaction solution is concentrated to get the solid having PAL-3 content is less than 1%.

Step (b)—Optional Recrystallization of the Compound Obtained in Step (a).

Palonosetron or its salt can be dissolved in suitable alcohol, alcohol such as methanol, ethanol, isopropyl alcohol, n-butanol, and the like, at a temperature of about 25° C. to about 65° C. and then isolated the solid by using conventional techniques such as cooling, partial removal of the solvent from the solution, anti solvent, seeding, or a combination thereof.

The obtained solution is optionally concentrated to an extent and cooled to suitable temperatures where the precipitation of the palonosetron or its salt begins from the solution, converting the solution into slurry.

The solution may be maintained further at a temperatures lower than the concentration temperatures such as for example below about 40° C., for a period of time as required for a more complete isolation of the product. The exact cooling temperature and time required for complete crystallization can be readily determined by a person skilled in the art and will also depend on parameters such as concentration and temperature of the solution or slurry.

The solid can be isolated by conventional techniques such as filtering, decanting, centrifuging and the like, or by filtering under an inert atmosphere using gases such as for example nitrogen and the like.

The solid may optionally be further dried. The drying can be carried out at temperatures of about 35° C. to about 70° C. The drying can be carried out for any desired time periods from about 1 to about 20 hours.

Optionally, the above described step (b) can be adapted to form the basis of a continuous crystallization process to get the S-isomer substantially free from its R-isomer and PAL-3.

Salts include acid addition salts formed with inorganic acids such as hydrochloric acid, hydrobromic acid, hydroiodic acid, sulfuric acid, nitric acid, phosphoric acid, and the like; or with organic acids such as acetic acid, propionic acid, hexanoic acid, heptanoic acid, malonic acid, succinic acid, malic acid, tartaric acid, citric acid, oxalic acid, and the like.

Palonosetron hydrochloride, provided by the process of this application has purity by high performance liquid chromatography ("HPLC") greater than or equal to about 99.5%. It has low levels of any one or more impurities. For example it contains less than about 0.15%, or less than about 0.01%, by weight of naphthoic acid of Formula II ("Impurity A");

Formula II

COOH less than about 0.15%, or less than about 0.01%, by weight of 5,6,7,8-tetrahydro-1-napthylene carboxylic acid of Formula III ("Impurity B");

Formula III

COOH less than about 0.15%, or less than about 0.01%, by weight of N—[(S)-1-Azabicyclo[2.2.2]oct-3-yl]-5,6,7,8-tetrahydronaphthylene-1-carboxamide of Formula IV ("Impurity C");

Formula IV less than about 0.2%, or less than about 0.04%, by weight of 2-[(S)-1-Azabicyclo[2.2.2]oct-3-yl]-2,4,5,6-tetrahydro-1H-benz[de]isoquinolin-1-one-HCl of Formula V ("Impurity D");

Formula V less than about 0.25%, or less than about 0.2%, by weight of (3aR)-[2-(S)-1-Azabicyclo[2.2.2]oct-3-yl]-2,3,3a,4,5,6-hexahydro-1H-benz[de]isoquinolin-1-one-HCl of Formula VI ("Impurity E");

Formula IV

Palonosetron hydrochloride obtained by the above process has been analyzed using high performance liquid chromatography ("HPLC") with the conditions described in Table 1.

TABLE 1

| Column and Packing: | Hichrom RPB, 250 × 4.6 mm, 5μ |
| --- | --- |
| Buffer | Dilute 0.670 ml of trifluoroacetic acid in 720 ml of Milli Q water, filter and degas. |
| Mobile Phase A: | Mix buffer and acetonitrile in the ratio of 75:25 (5 v/v) |
| Mobile Phase B: | Mix buffer and acetonitrile in the ratio of 50:50 (% v/v) |

| | Time (minutes) | Solution A (% v/v) | Solution B (% v/v) | Elution |
| --- | --- | --- | --- | --- |
| Gradient: | 0 | 100 | 0 | Isocratic |
| | 18 | 100 | 0 | Isocratic |
| | 40 | 50 | 50 | Linear gradient |
| | 45 | 30 | 70 | Linear gradient |
| | 50 | 100 | 0 | Re-equilibration |
| | 55 | 100 | 0 | Equilibration |

| Flow rate: | 1.0 ml/minute |
| --- | --- |
| Wavelength of detection: | 240 nm by UV |
| Temperature: | 25 ± 2° C. |
| Injection volume: | 10 μL |
| Diluent: | Mobile phase A |
| Run time: | 55 minutes |

The relative retention times ("RRT") of impurity peaks are given below in Table 2, where palonosetron is assigned the value of 1.

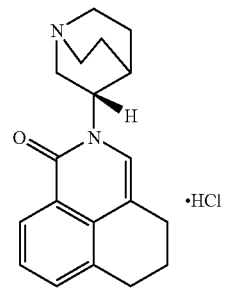
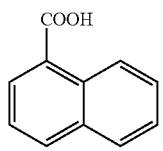
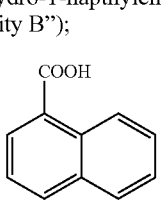
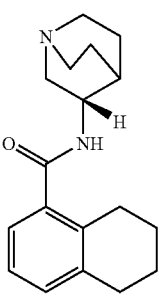

TABLE 2

| Impurity | RRT |
| --- | --- |
| Palonosetron | 1.00 |
| Impurity A | 3.12 |
| Impurity B | 2.67 |
| Impurity C | 0.70 |
| Impurity D | 0.90 |
| Impurity E | 0.93 |

The crystalline polymorphs obtained by the process of present application, unless stated otherwise, are characterized by their X-ray powder diffraction ("XRPD") patterns, differential scanning calorimetry ("DSC") curves, and termogravimetric analysis (TGA) curves.

Differential scanning calorimetric analysis was carried out in a DSC Q1000 instrument from TA Instruments with a ramp of 10° C./minute with a modulation time of 60 seconds and a modulation temperature of ±1° C. The starting temperature was 0° C. and ending temperature was 200° C.

XRPD data reported herein were obtained using Cu Kα radiation, having the wavelength 1.541 Å and were obtained using a Bruker AXS D8 Advance Powder X-ray Diffractometer.

TGA analysis was carried out in a TGAQ500V64 Build 193 instrument with a ramp 10° C./minute up to 250° C.

In another embodiment, the present invention provides the crystalline form of palonosetron hydrochloride characterized by having differential scanning calorimetry (DSC) thermogram having endotherm peak at 306.83° C.

In another embodiment the invention provides the crystalline form of palonosetron hydrochloride characterized by having X-ray diffraction pattern with characteristic peaks at diffraction angles 2-theta of about 7.1, 13.8, 14.2, 15.8, 18.5, 19.7, 20.0 and 24.4±0.2 degrees.

In another embodiment of the invention, the crystalline form of palonosetron hydrochloride is characterized by having TGA curve corresponding to a weight loss of about 0.120% (0.011 mg).

In one embodiment of the present invention, there is provided a palonosetron hydrochloride crystalline form characterized by having substantial purity. The crystalline form of the present application may contain less than about 0.5%, or less than about 0.1% of the structure related impurities as characterized by a high performance liquid chromatography ("HPLC").

In yet another embodiment the invention provides palonosetron hydrochloride substantially free of residual solvents.

Palonosetron hydrochloride obtained using the process of the present application has amount of residual solvent content that is within the limits given by the International Conference on Harmonization of Technical Requirements for Registration of Pharmaceuticals for Human Use ("ICH") guidelines. The guideline solvent level depends on the type of solvent but is not more than about 5000 ppm, or about 4000 ppm, or about 3000 ppm.

The palonosetron hydrochloride obtained in this application contains: less than about 800 ppm, or less than about 1000 ppm of methanol; less than about 100 ppm, or less than about 500 ppm of ethanol; less than about 100 ppm, or less than about 500 ppm of isopropyl alcohol; less than about 100 ppm, or less than about 500 ppm of ethyl acetate; less than about 100 ppm, or less than about 500 ppm of toluene; less than about 100 ppm, or less than about 250 ppm of petroleum ether; less than about 100 ppm, or less than about 500 ppm of tetrahydrofuran; less than about 100 ppm, or less than about 500 ppm of N,N-dimethylformamide; less than about 100 ppm, or less than about 500 ppm of acetic acid.

The dried product can optionally be milled to get the required particle size. Milling or micronization can be performed prior to drying, or after the completion of drying of the product. The milling operation reduces the size of particles and increases surface area of particles by colliding particles with each other at high velocities.

In another embodiment, the present invention provides palonosetron hydrochloride polymorph obtained from present application, which are stable and are well suited for use in preparing pharmaceutical formulations. The pharmaceutical formulations according to the present application include but are not limited to solid oral dosage forms such as tablets, capsules, powders and so on; liquid oral dosage forms such as solutions, dispersions, suspensions, emulsions and so on; parenteral dosage forms (including intramuscular, subcutaneous, intravenous) such as injectable dosages by solution or suspension or dispersions or sterile powders for reconstitution; transdermally delivery systems; targeted delivery systems etc.

Certain specific aspects and embodiments of the present application will be explained in more detail with reference to the following examples, which are provided by way of illustration only and should not be construed as limiting the scope of the application in any manner.

EXAMPLES

Example 1

Process for Preparing Palonosetron Hydrochloride

PAL-3 (60 g) was suspended in ethanol (600 ml) and palladium on carbon (50% wet, 60 g) was suspended in ethanol (600 ml). Both the Pd/C—ethanol suspensions and the reaction solution were charged simultaneously into a clean and dry autoclave at a temperature of about 25° C. to about 30° C. Nitrogen gas and vacuum was applied to the reaction mixture. Hydrogen gas pressure (100 Psi) was passed into the reaction mixture and then released. Dry hydrogen gas pressure (400 Psi) was passed again into the reaction suspension and the reaction mixture was heated to a temperature of about 55° C. to 60° C. The reaction mixture was stirred for about 48 hours at a temperature of about 55° C. to about 60° C. under hydrogen gas pressure of about 400 Psi. After the completion of the reaction, the stirring was stopped and the catalyst was allowed to settle in the reaction mixture for about 2 hours followed by releasing of hydrogen gas pressure for a period of about 1 hour. The reaction mass was removed through sampler tube and then filtered on celite at a temperature of about 55° C. to about 60° C. The resultant filtrate was distilled completely at a temperature of about 55° C. to about 60° C. under high vacuum (450-680 mm Hg) to afford 40 g of title compound with purity by chiral HPLC: 52.61% w/w of S-isomer, 45.19% w/w of R-isomer and 0.65% w/w of PAL-3.

Example 2

Recrystalization Process for Palonosetron Hydrochloride

Palonosetron hydrochloride (85 g), prepared accordingly by Example 1, was suspended in ethanol (255 ml) and stirred for about 2 hours at a temperature of about 25° C. to about 35° C. The resultant suspension was filtered and washed with ethanol (70 ml), and then suck dried for about 3 hours to afford 32 g of palonosetron hydrochloride with purity by chiral HPLC: 93.71% w/w of S-isomer, 6.13% w/w of R-isomer, 0.08% w/w of PAL-3.

The above-obtained compound was suspended in methanol (30 ml) at a temperature of about 25° C. to about 30° C. and stirred for about 10 minutes, and then distilled completely at a temperature of about 55° C. to about 60° C. Methanol (52.5 ml) was added to the obtained solid and stirred for about 15 minutes at a temperature of about 55° C. to about 60° C., and the suspension level was marked. Methanol (122 ml) was added to the above suspension and stirred for about 30 minutes. The reaction solution was filtered through celite to separate the small particles and the celite bed was washed with methanol (15 ml). Clear filtrate was concentrated upto the marked level and cooled to a temperature of about 25° C. to about 35° C. with simultaneous stirring for a period of about 1 hour. The reaction mass was stirred for about 1 hour at a temperature of about 25° C. to about 35° C. and then cooled to a temperature of about 0° C. to about 5° C., and stirred for about 2 hours at a temperature of about 0° C. to about 5° C. The suspension was filtered and the solid was washed with precooled methanol (35 ml). The solid was suck dried over a period of about 30 minutes under vacuum of about 680 mmHg and then dried at a temperature of about 50° C. for about 24 hours to afford title compound with purity by chiral HPLC of 99.72% w/w of S-isomer, 0.18% w/w of R-isomer, 0.04% w/w of PAL-3.

Example-3

Reprocess for Purification of Palonosetron Hydrochloride (Formula I)

Palonosetron hydrochloride (95 g), having more than 1% of PAL-3, was suspended in ethanol (285 ml) and stirred for about 2 hours at a temperature of about 25° C. to about 35° C. The resultant suspension was filtered and washed with ethanol (95 ml) to afford palonosetron hydrochloride (45 g) with purity by chiral HPLC of 90.84% w/w of S-isomer, 5.10% w/w of R-isomer, 3.92% w/w of 2-[(s)-1-Azabicyclo[222]oct-3-yl]-2,4,5,6-tetrahydro-1H-benz[de]isoquinolin-1-one hydrochloride.

Palonosetron hydrochloride (45 g) with a chiral purity of about 90.84% was suspended in methanol (400 ml) while preparing the suspension of Pd/C using 10% of Pd/C (45 g) in methanol (400 ml). Both resultant suspensions were charged into autoclave and stirred for about 10 min. Hydrogen gas was applied to the above autoclave at pressure 60 Psi and the temperature was raised to about 55° C. to about 60° C. The reaction mass was stirred for about 24 hours at a temperature of about 50° C. to about 60° C. while maintaining the hydrogen pressure at a temperature of about 50° C. to about 60° C. The reaction mass was cooled to a temperature of about 25° C. to about 30° C. and the hydrogen gas was released followed by decanting of the reaction mass. The reaction mass was then filtered on celite and the celite was washed with 100 ml methanol. The resultant filtrate was distilled completely at a temperature of about 50° C. to about 60° C. under high vacuum of about 450 to 680 mm Hg. The compound obtained was dissolved in methanol (150 ml) at a temperature of about 50° C. to about 60° C. and the methanol (60 ml) was distilled off from solution. The resultant reaction solution was cooled to a temperature of about 0° C. to about 5° C. followed by stirring for about 4 hours. The separated solid was filtered and the solid was washed with precooled methanol (30 ml). The solid obtained was dissolved in methanol (90 ml) at a temperature of about 50° C. to about 60° C. followed by distillation of methanol (36 ml). The resultant reaction solution was cooled to a temperature of about 0° C. to about 5° C. followed by stirring for about 4 hours. The separated solid was filtered and was washed with methanol (18 ml) at a temperature of about 45° C. to about 50° C. to afford title compound with purity by chiral HPLC 99.75%.

The invention claimed is:

1. A crystalline form of palonosetron hydrochloride characterized by having X-ray powder diffraction pattern with principal peaks approximately at 7.1, 13.8, 14.2, 15.8, 18.5, 19.7, 20.0 and 24.4±0.2 degrees 2 theta.

2. Palonosetron hydrochloride of claim 1 substantially free of (3aR)-[2-(S)-1-azabicyclo[2.2.2]oct-3-yl]-2,3,3a,4,5,6-hexahydro-1H-benz[de]isoquinolin-1-one-HCl (R-isomer) and 2-[(S)-1-azabicyclo[2.2.2]oct-3-yl]-2,4,5,6-tetrahydro-1H-benz[de]isoquinolin-1-one HCl (PAL-3).

3. The palonosetron hydrochloride of claim 2, having purity equal to or greater than 99.5%.

4. The palonosetron hydrochloride of claim 2 wherein said R-isomer content is less than 0.2%.

5. The palonosetron hydrochloride of claim 2, wherein said PAL-3 content is less than 0.2%.

6. The palonosetron hydrochloride of claim 2, having less than 0.2% of each of R-isomer and PAL-3.

Figure 2:
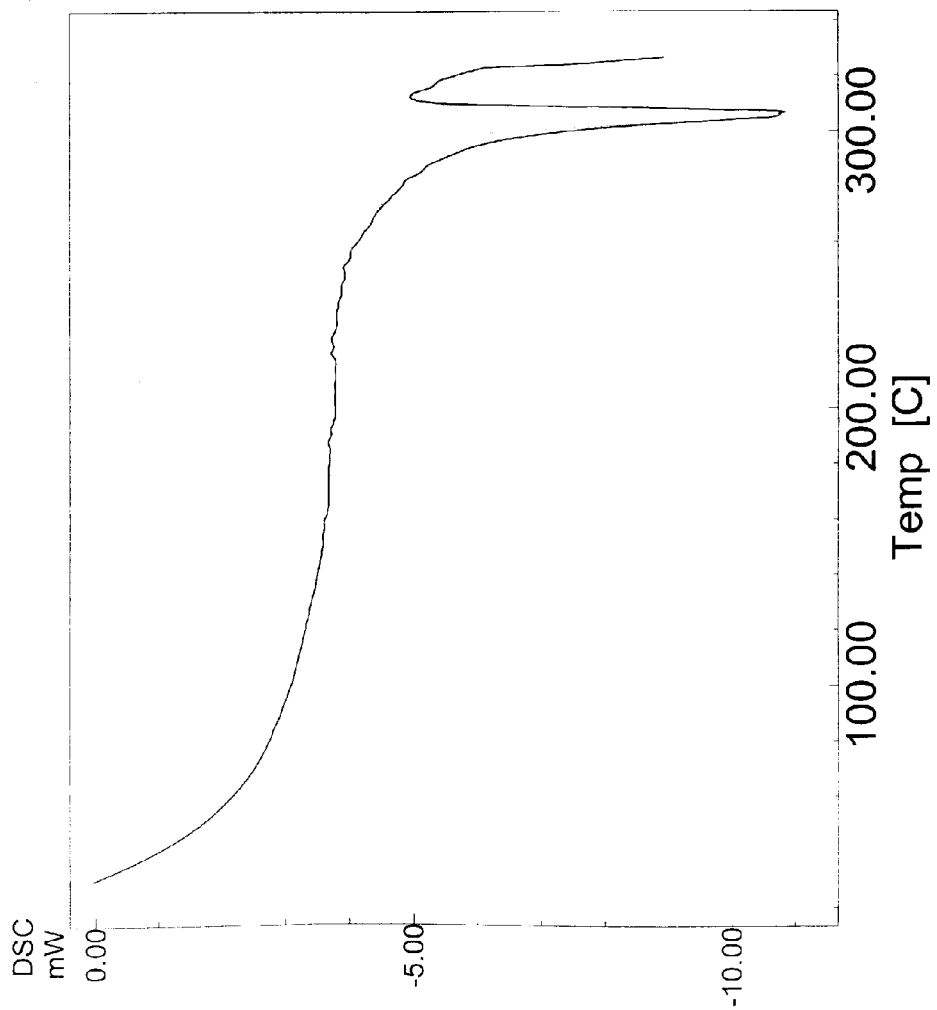
FIG. 2 is a differential scanning calorimetry ("DSC") curve of palonosetron hydrochloride crystalline form prepared according to Example 3.
Figure 3:
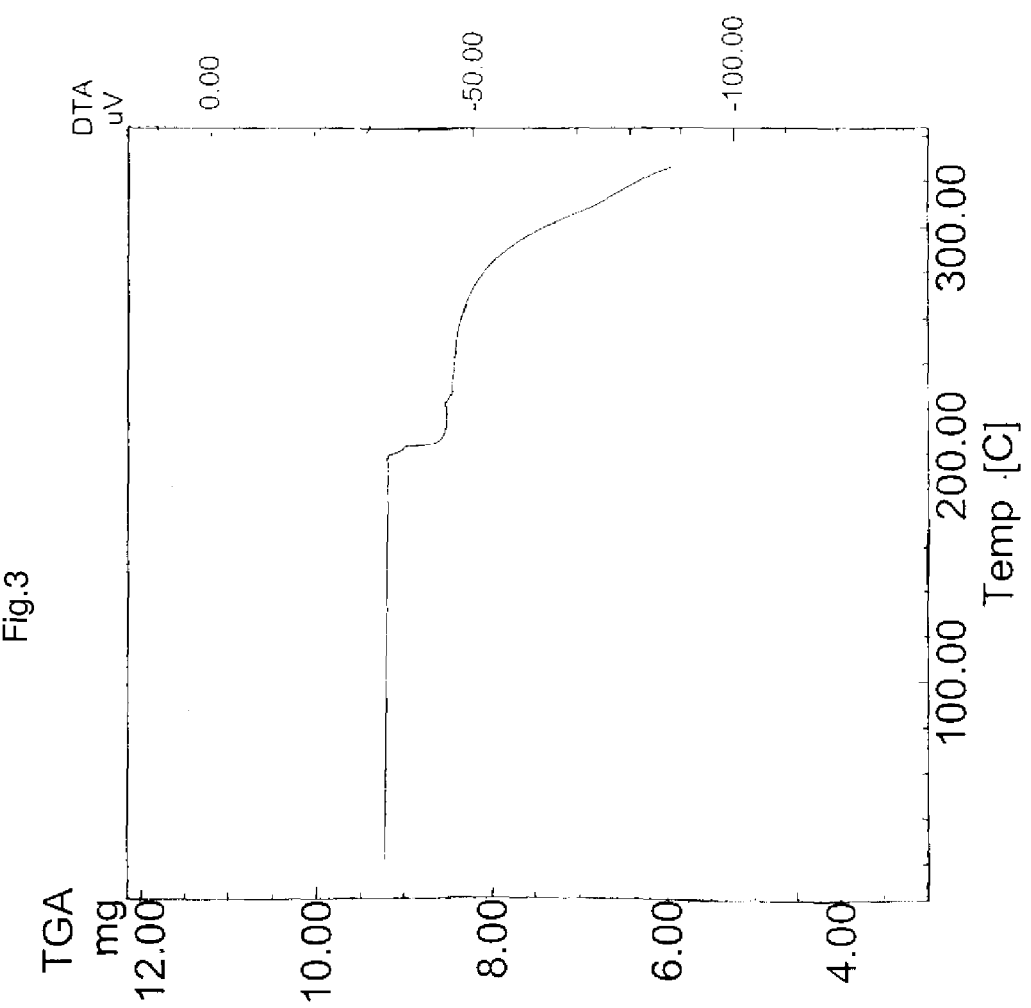
FIG. 3 is a thermogravimetric analysis (TGA) curve of palonosetron hydrochloride crystalline form.

7. A crystalline form of palonosetron hydrochloride as given in claim 1, having an endotherm peak at 306.83° C. by differential scanning calorimetry, which is substantially in accordance with FIG. 2.

8. A pharmaceutical composition comprising the crystalline form of palonosetron hydrochloride according to claim 2, together with one or more pharmaceutically acceptable excipients.

9. The pharmaceutical composition of claim 8 which are useful in the treatment of emesis.

10. A pharmaceutical composition comprising the crystalline form of palonosetron hydrochloride according to claim 1, together with one or more pharmaceutically acceptable excipients.

11. The pharmaceutical composition of claim 10 which are useful in the treatment of emesis.

12. A pharmaceutical composition comprising the crystalline form of palonosetron hydrochloride according to claim 7, together with one or more pharmaceutically acceptable excipients.

13. The pharmaceutical composition of claim 12 which are useful in the treatment of emesis.

* * * * *